United States Patent
Stuebner et al.

(10) Patent No.: US 6,809,249 B2
(45) Date of Patent: Oct. 26, 2004

(54) SELF-ALIGNING ULTRASONIC DISPLACEMENT SENSOR SYSTEM, APPARATUS AND METHOD FOR DETECTING SURFACE VIBRATIONS

(75) Inventors: Fred Stuebner, Lagrangeville, NY (US); Jesse Aronstein, Poughkeepsie, NY (US)

(73) Assignee: Protune Corp., Poughkeepsie, NY (US)

( * ) Notice: Subject to any disclaimer, the term of this patent is extended or adjusted under 35 U.S.C. 154(b) by 153 days.

(21) Appl. No.: 09/683,502

(22) Filed: Jan. 9, 2002

(65) Prior Publication Data

US 2003/0005816 A1 Jan. 9, 2003

Related U.S. Application Data

(60) Provisional application No. 60/261,722, filed on Jan. 12, 2001.

(51) Int. Cl.$^7$ ................................................. G10H 1/02
(52) U.S. Cl. ............................................................. 84/738
(58) Field of Search ...................................... 84/723, 738

(56) References Cited

U.S. PATENT DOCUMENTS

| | | | | |
|---|---|---|---|---|
| 3,595,084 A | * | 7/1971 | Bailey et al. ............... | 73/866.5 |
| 3,955,459 A | * | 5/1976 | Mochida et al. ............ | 84/609 |
| 4,023,462 A | * | 5/1977 | Denov et al. ................ | 84/454 |
| 4,453,448 A | * | 6/1984 | Miesak ........................ | 84/454 |
| 4,457,203 A | * | 7/1984 | Schoenberg et al. ........ | 84/454 |
| 4,589,324 A | * | 5/1986 | Aronstein .................... | 84/454 |
| 4,702,112 A | * | 10/1987 | Lawrie et al. ............... | 73/629 |
| 4,741,242 A | * | 5/1988 | Aronstein .................... | 84/454 |
| 4,926,693 A | * | 5/1990 | Holm-Kennedy et al. .... | 73/597 |
| 5,024,134 A | * | 6/1991 | Uchiyama .................... | 84/654 |
| 5,123,324 A | * | 6/1992 | Rose et al. ................... | 84/726 |
| 5,155,212 A | * | 10/1992 | Dubler et al. ............... | 530/380 |
| 5,272,908 A | * | 12/1993 | Soss ........................... | 73/35.14 |
| 5,345,037 A | * | 9/1994 | Nordelius .................... | 84/730 |
| 5,355,130 A | * | 10/1994 | Luber ......................... | 340/870.14 |
| 5,373,742 A | * | 12/1994 | Terhune ....................... | 73/606 |
| 5,457,640 A | * | 10/1995 | Foller et al. ................. | 702/56 |
| 5,719,344 A | * | 2/1998 | Pawate ........................ | 84/609 |
| 5,804,698 A | * | 9/1998 | Belonenko et al. .......... | 73/1.83 |
| 5,808,177 A | * | 9/1998 | Bonnefoy .................... | 73/1.82 |
| 6,278,047 B1 | * | 8/2001 | Cumberland ................. | 84/455 |
| 6,317,169 B1 | * | 11/2001 | Smith .......................... | 348/744 |

OTHER PUBLICATIONS

Young, C. W., et al., "An Advance Utrasonic System for Vibration Measurement," Advances In Instrumentation and Control, Instrument Society of America, Research Triangle Park, US, vol. 51, No. Part 2, 1996, pp. 811–816, XP000639424, ISSN: 1054–0032.

Persson, H. W. et al., "Remote Vibration Measurements Using Airborne Ultrasound," Ultrasonics Symposium, 1996, Proceedings, 1996 IEEE San Antonio, TX USA Nov. 3–6, 1996, New York, NY, USA, IEEE, US, Nov. 3, 1996, pp. 689–892, XP010217807, ISBN: 0–7803–3615–1.

Bou Matar O., et al., "Performances of the Parametric Acoustic Vibrometer for Vibration Sensing," Ultrasonics Symposium, 1997, Proceedings, 1997 IEEE Toronto, Ontario, Canada, Oct. 5–8, 1997, New York, NY, USA, IEEE, US, Oct. 5, 1997, pp. 605–608, XP010271329, ISBN: 0–7803–4153–8.

* cited by examiner

*Primary Examiner*—Jeffrey W Donels
(74) *Attorney, Agent, or Firm*—Jay R. Yablon

(57) ABSTRACT

Ultrasonic transducing elements (11, 12) are used to measure vibrations of a nearby musical drumhead or other vibrating surface (13). A first ultrasonic transducer (11) emits an ultrasonic signal (14) and a second ultrasonic transducer (12) listens for an echo of that signal (14). A phase change of the echoed (reflected) signal (202) is compared to a reference signal (206) to create a representation signal (216) which represents the movement of the drumhead or other vibrating surface (13). For this comparison to be properly made, a deviation signal (220) is generated that defines an average deviation of the reference signal (206) from optimum, which is then used to self-align the reference signal (206) to the reflected signal (202).

68 Claims, 4 Drawing Sheets

SELF-ALIGNING ULTRASONIC DISPLACEMENT SENSOR SYSTEM, APPARATUS AND METHOD FOR DETECTING SURFACE VIBRATIONS

CROSS REFERENCE TO RELATED APPLICATIONS

This application claims the benefit of U.S. Provisional Application No. 60/261,722, filed Jan. 12, 2001.

BACKGROUND OF INVENTION

This invention relates generally to vibration sensing, and specifically to sensing musical drumhead vibrations using an ultrasonic transducing element.

This invention comprises a device that permits sensing of surface vibrations by use of reflected sound at a frequency substantially higher than that of the surface vibrations to be sensed. One important application is for sensing drumhead vibrations of a tunable drum so as to provide a signal to a sound analyzer that displays to the drum's player the note that is being played and the accuracy of its pitch relative to the standard musical scale.

Present sensing devices for this purpose utilize electromagnetic, optical, or acoustic methods that operate without contacting the drumhead, or piezoelectric or other methods that require the sensing element to be in physical contact with the drumhead. Each of these methods has its deficiencies insofar as pickup of extraneous signals such as "AC hum" (from electrical environment or from the room lighting) or room ambient sound, requiring use of a separate "target" that must be attached to the drumhead, direct contact with the drum head, and/or difficult setup and calibration/alignment.

SUMMARY OF INVENTION

Ultrasonic transducing elements are used to measure vibrations of a nearby musical drumhead or other vibrating surface. A first ultrasonic transducer emits an ultrasonic signal and a second ultrasonic transducer listens for an echo of that signal. A phase change of the echoed (reflected) signal is compared to a reference signal to create a representation signal which represents the movement of the drumhead or other vibrating surface. For this comparison to be properly made, a deviation signal is generated that defines an average deviation of the reference signal from optimum, which is then used to self-align the reference signal to the reflected signal.

The disclosed invention is capable of operating at a relatively large distance from the drumhead. It does not contact the drumhead nor does it require a special target to be placed on the drumhead. It does not require any specialized setup, does not contact the drumhead, and is insensitive to interference from room ambient sound, electromagnetic signals, lighting/optical signals, or temperature changes. All of these are significant advantages relative to presently-used vibration sensing methods. Ease of installation is another major advantage. To use the sensor, it is simply fixtured in place with its active elements facing the drumhead. Within a large operating range, the sensor system automatically compensates (self-aligns) for differences in the set operating distance to the drum head, air temperature, and other variables.

BRIEF DESCRIPTION OF DRAWINGS

The features of the invention believed to be novel are set forth in the appended claims. The invention, however, together with further objects and advantages thereof, may best be understood by reference to the following description taken in conjunction with the accompanying drawing(s) in which:

DETAILED DESCRIPTION

The Ultrasonic Displacement Sensor is a device that detects the motion of a vibrating surface, such as but not limited to a drumhead, toward or away from the sensor itself. For sensing timpani drumhead or other tunable instrument vibrations such as is described in commonly-assigned and invented U.S. Pat. No. 4,741,242, a range of interest is about 20 to 1000 Hz, which in this disclosure will be characterized generally as vibrational frequencies in the range of less than approximately 1 kHz. For sensing vibrations of other surfaces or objects, it is understood that different ranges of vibrational frequency may be of interest.

For sensing drumhead vibrations, the sensor consists of two ultrasonic transducers operating at about 40 kHz, which, in particular, thus operate at a frequency about 40 times higher than the highest vibrational frequency of interest to be detected from the drumhead. One of these ultrasonic transducers emits the 40 kHz tone, and the second listens for an echo from the drumhead. For sensing vibrations generally, the ultrasonic transducers utilized should operate at a frequency substantially higher (e.g., optimally at least 40 times as high, preferably as high as possible without limitation consistent with transducer technology and cost, but at least 10 to 20 times as high) than the highest vibrational frequency of interest for detection. With this general understanding that the optimum transducer frequency will depend on the upper range of the vibrational frequencies of interest, the ultrasonic transducers used in this disclosure for purposes of illustration will be characterized as operating at approximately 40 kHz.

Figure 1:
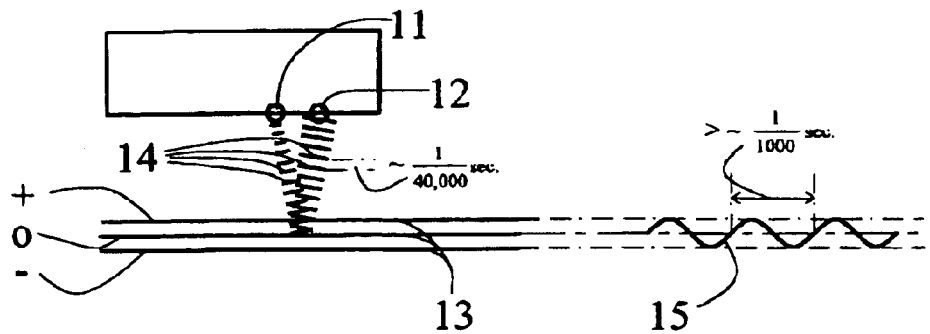
FIG. 1 is a side plan view illustrating the placement of the ultrasonic transducer relative to a vibrating surface such as a drumhead, and schematically illustrating the emission and reception of ultrasonic signal as well as the vibration of the vibrating surface.

In a preferred embodiment illustrated in FIG. 1, the emitting 11 and receiving 12 transducers are located approximately 2 inches (i.e. 5 cm) away from the vibrating surface 13 such as a drumhead, and are preferably angled and set to focus on a substantially single spot (as focused a beam as possible is preferred consistent with available transducer technology and cost, but is not required) approximately the same 2 inch (5 cm.) distance as the drum head. This maximizes the reflected signal from this one point, and thereby diminishes the contribution of any other reflection, in essence focusing the sensing to a smaller spot. Vibrating surface 13 is illustrated in a "o" quiescent position, as well as in a "+" position at the highest point of its vibration and a "−" position at the lowest point of its vibration. The ultrasonic emissions 14 are illustrated to be operating at approximately 40 kHz (i.e., spaced from one another by ∼1/40,000 sec), and the vibrations 15 of vibrating surface 13 (e.g., the drumhead) from high point + to low point are illustrated to be in the range of less than approximately 1 kHz (i.e., vibrating with a cycle time >∼1/1000 sec).

Although these sensors in the preferred embodiment are located approximately 2 inches (5 cm.) away and angled as described above so that their centerlines meet at a point about 2 inches (5 cm.) away from the transducer face, and the nominal setup of the pickup is then 2 inches (5 cm.) from the head, they are capable of being placed approximately eight inches (20 cm), one foot (30 cm), or even three or more feet (approximately 1 or more meters) away. They can also be placed less than an inch (2.5 cm.) and even as close as about ¼ inch (approximately 5 mm) away and still maintain an effective signal. Additionally, the converging of the transducer centerlines at the vibrating surface is preferred, but not a necessary feature.

The sensors are placed proximate the vibrating surface 13, e.g., drumhead as described above, with their active elements facing the drumhead, either outside the drum as illustrated in, e.g., FIG. 7 of U.S. Pat. No. 4,741,242, or inside the drum so as to be hidden from view. The stronger the reflected signal is, the less chance there is for a false reflection to influence the signal. Thus, any setup which optimizes the strength of the reflected signal is preferred.

Figure 2:
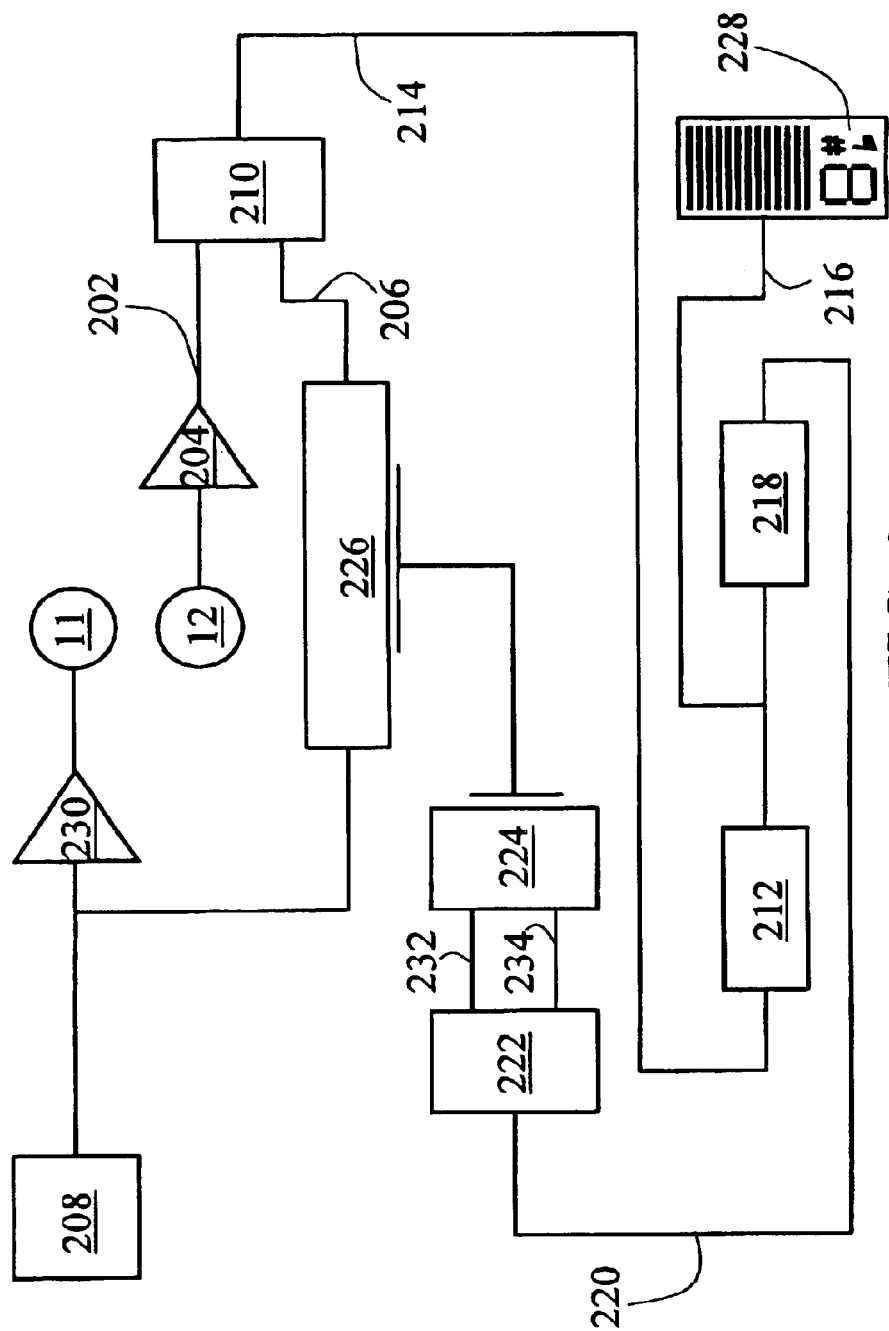
FIG. 2 is a block diagram of the circuit disclosed herein for processing the transducer signals to sense the vibration of the surface and for self-aligning the overall system.

It is the change in phase of the returned 40 kHz echo that is measured to determine the movement of the drumhead or other vibrating surface 13. As illustrated in FIG. 2, the phase of the reflected signal 202 received by receiving transducer 12 and emerging from amplifier 204 is compared to a reference signal 206 originating from and driven by a timing signal from oscillator 208 using a comparator (e.g. exclusive OR) circuit 210 to generate comparison signal 214. Comparison signal 214 is then passed through a low pass filter 212 which only passes through frequencies below a low pass threshold of approximately 1 kHz (and more generally, below the highest vibrational frequency of interest) to create a representation signal 216 which represents the movement of the vibrating surface. Amplified 230 output from oscillator 208 also drives emitting transducer 11. (The exclusive OR circuit 210 illustrated as an example drives its output high when both inputs are high and also when both inputs are low, and it drives its output low when one input is high while the other input is low. It is understood that an exclusive OR inverse to this is also feasible within the scope of this disclosure and its associated claims.) For the exclusive OR comparator 210 to work properly, the phase of the reference signal 206 must be adjusted so that it is optimum when the vibrating surface is at its center (non-displaced, equilibrium) "o" point. This is accomplished by using a second, "low-low" pass filter 218 with cutoff frequency at 1 Hz (and generally, substantially below the lowest vibrational frequency of interest) to generate a deviation signal 220 that defines the average deviation of the reference signal 206 from optimum. This deviation signal 220 is used in combination with gating logic 222, an up/down counter 224 (with illustrated up input 232 and down input 234) and a delay device 226 such as a shift register, to self-align (i.e. self-calibrate) the reference signal 206 originating from oscillator 208 relative to the reflected signal 202, prior to their being compared with exclusive OR circuit 270. This is done by stepping counter 224 up or down as required to select the correct delay via delay device 226 and thereby provide optimal sensitivity. While FIG. 2 illustrates deviation signal 220 being derived directly from representation signal 276 and indirectly from comparison signal 214 with low pass filter 272 and low-low pass filter 278 in series, it is understood that deviation signal 220 may also be derived directly from comparison signal 214 by placing low pass filter 212 and low-low pass filter 218 in parallel with one another. The key point is that deviation signal 220 is in any event derived from comparison signal 214, whether directly without low pass filter 212 intervening, or indirectly as illustrated in FIG. 2 with low pass filter 212 intervening. Thus, in general terms, whether directly or indirectly, deviation signal 220 is extracted by passing through from comparison signal 214, frequencies lower than the low-low pass threshold established by low-low pass filter 218.

Representation signal 216, which represents the actual vibrational movement of vibrating surface 13, may then be provided to a vibrational information display device 228 in order to provide human-readable information about this vibrational movement. Display device 228 can present this information in any form that is suitable to the application. For drumhead vibration, vibrational information display device 228 may, for example, comprise vibrational display means for displaying the note sounded and its pitch relative to a preset standard so as to indicate to the player whether or not the drum is set to the desired pitch, such as the display device disclosed and claimed in commonly-owned and invented U.S. Pat. No. 4,589,324. The display device disclosed and claimed in U.S. Pat. No. 4,589,324 displays one of the alphabetic characters A, B, C, D, E, F and G representing a musical note corresponding with said vibration of said surface 13; a musical sharp note indicator if said musical note is sharp; a musical flat note indicator if said musical note is flat; and a degree to which said musical note is out of tune using an out-of-tune indicator such as a plurality of spaced-apart strobe bar indicators.

To further illustrate the inherent operational properties of the circuit disclosed in FIG. 2, FIGS. 3 through 6 illustrate reference signal 206, reflected signal 202, comparison signal 214, representation signal 216, and deviation signal 220, produced by this circuit, in various operational situations. Reference signal 206, reflected signal 202, and comparison signal 214 are represented as "square" waves simply for simplicity.

Figure 3:
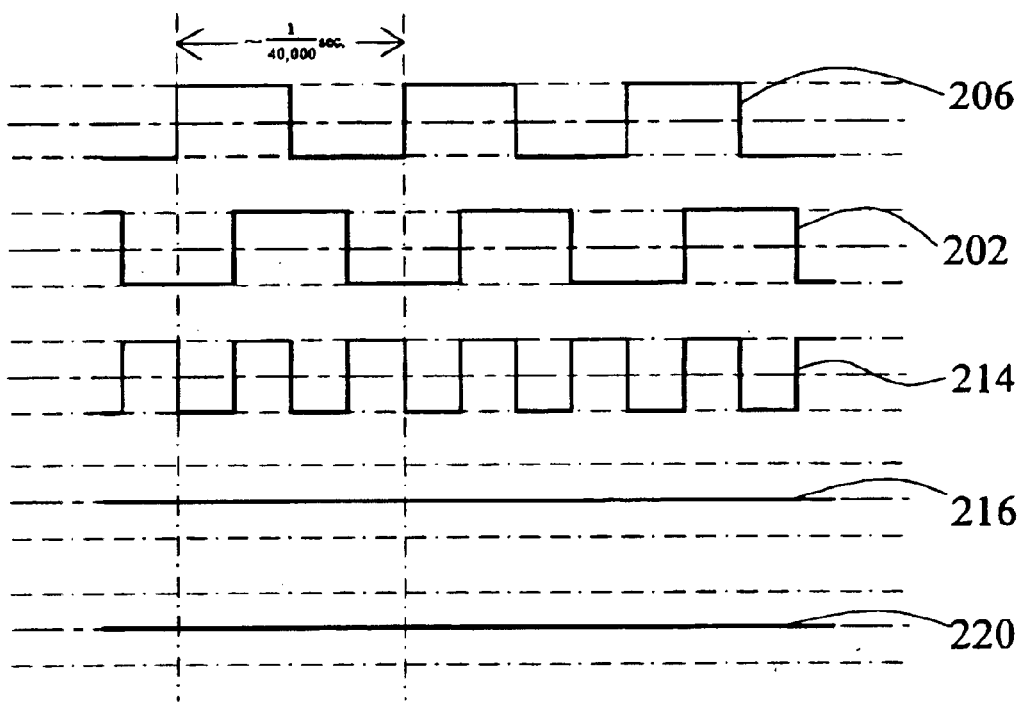
FIG. 3 illustrates the signals at various junctures of the circuit of FIG. 2, when the drumhead or similar surface is quiescent (not vibrating), and when the system is optimally aligned/calibrated.

FIG. 3 illustrates all of the reference signal 206, reflected signal 202, comparison signal 214, representation signal 216, and deviation signal 220 inherently produced by the circuit of FIG. 2, when the drumhead or similar surface is quiescent (not vibrating), and when the system is optimally aligned/calibrated. As noted earlier, the phase of the reference signal 206 must be adjusted so that it is optimum when the vibrating surface is at its center (non-displaced, equilibrium) "o" point. In detailed operational terms, this means that it is desired to maintain the phase of reference signal 206 one-quarter of a cycle ahead of the phase of reflected signal 202, as shown in FIG. 3. By maintaining a quarter-cycle separation between reference signal 206 and reflected signal 202, comparison signal 214 emerging from exclusive OR comparator circuit 210 cyclically runs high (+) half the time and low (−) half the time at twice the transducer frequency. Most importantly, this means that the average value of comparison signal 214 will be quiescent (o), when averaged over any time frame substantially larger than the time frame of a single transducer cycle. Thus, when comparison signal 214, which has an 80 kHz frequency, is run through the 1 kHz low pass filter 212, representation signal 216 will be flat, and it will also be centered at the quiescent (o) amplitude. This is precisely what is desired, because 1) the drumhead is quiescent and so the representation signal 216 representing its movement should also show quiescence, and 2) the system is calibrated about the "o" point. Deviation signal 220 emerging from low-low pass filter 218 is also flat and centered at the quiescent (o) amplitude, designating proper calibration for reasons to be discussed further below.

Figure 4:
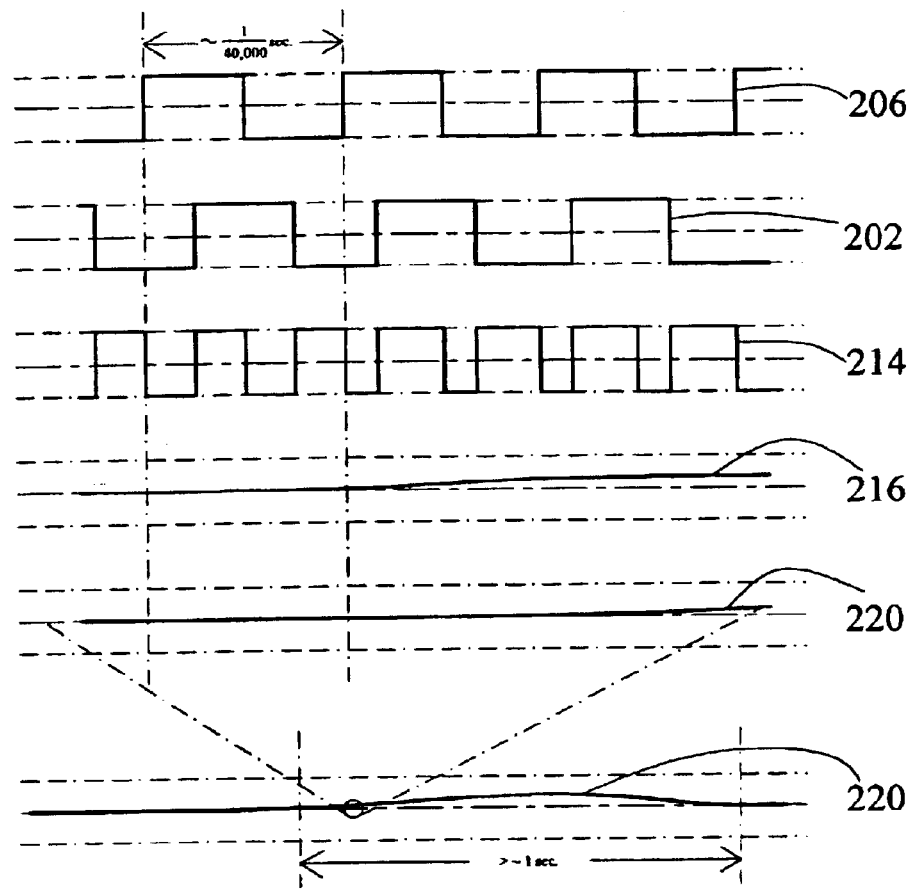
FIG. 4 illustrates the signals at various junctures of the circuit of FIG. 2, when the drumhead or similar surface is quiescent (not vibrating), but when the system moves out of optimum alignment/calibration. As also illustrated by FIG. 4, the detection that the system is out of alignment/calibration is used as the basis for self-aligning the system back into the proper calibration, and is used to self-calibrate the system during its initial setup.

FIG. 4 illustrates all of the reference signal 206, reflected signal 202, comparison signal 214, representation signal 216, and deviation signal 220 inherently produced by the circuit of FIG. 2, when the drumhead or similar surface is quiescent (not vibrating), but when the system moves out of optimum alignment/calibration. The detection that the system is out of alignment/calibration is used as the basis for self-aligning the system back into the proper calibration during operation, and is also used to self-calibrate the system during its initial setup. In the illustration of FIG. 4, it is assumed that for some reason, the distance between the drumhead 13 and the transducers 11 and 12 is suddenly, slightly reduced. Such a reduced distance implies that reflected signal 202 will return to receiving,transducer 12 slightly sooner than it would have returned before this sudden reduction in distance. This is represented by the fact that in FIG. 4 the second "−" region of reflected signal 202 has been drawn so as to of a slightly shorter temporal duration (by a ⅚ factor) than any of the other + or regions of reflected signal 202, as may be observed by a careful perusal of FIG. 4. Because of this shift, comparison signal 214 emerging from exclusive OR circuit 210 changes after its third + pulse, and it now spends approximately ⅔ of its time in the + state and ⅓ of its time in the state. As a consequence, the average value of comparison signal 214 is now ⅔ of the way toward the + state and away from the state. This average value is captured in a rise in the representation signal 216 emerging from low pass filter 212, again, because low pass filter 212 cuts off frequencies at a frequency substantially below the transducer frequency (1 kHz cutoff compared to 40 kHz transducers for the illustrated embodiments). Deviation signal 220 will also rise over time to be ⅔ of the way toward the + state and away from the state. However, since deviation signal 220 emerges from low-low pass filter 218 which has a 1 Hz (i.e. 1 cycle per second) cutoff in this particular embodiment and a cutoff below all vibrational frequencies of interest generally, it will take much more time for low-low pass filter 218 to fully respond to this rise, and in particular, it will take on the order of one to several seconds to respond. This is illustrated by the upward-sloping portion of the bottom-most representation of deviation signal 220, which is drawn to a much larger (~1 second) time scale than the remainder of FIG. 4.

Referring again to FIG. 2, it is deviation signal 220 that feeds in to gating logic 222, up/down counter 224 and delay device 226 to self-align (i.e. self-calibrate) the reference signal 206 originating from oscillator 208 relative to the reflected signal 202. In particular, gating logic 222, up/down counter 224 provide shift calculation means for determining how much and in which direction the timing signal from oscillator 208 needs to be temporally shifted in order to get back into proper phase with reflected signal 202, and delay device 226 provides means for actually advancing or delaying (shifting) the provision of timing signal from oscillator 208 to comparator circuit 210 as reference signal 206. Thus, once deviation signal 220 strays from the central "o" quiescent state, gating logic 222, up/down counter 224 and delay device 226 provide one embodiment of a combined self-calibration/self-adjustment means for recalibrating reference signal 206 back into the optimally aligned/calibrated phase of FIG. 3, relative to reflected signal 202. This recalibration is illustrated by the downward-sloping portion of the bottom-most representation of deviation signal 220 in FIG. 4. Once the recalibration is completed, deviation signal 220 returns to its central "o" quiescent state of FIG. 3. In light of this, it is apparent that FIG. 3 defines the proper "objective" for calibration.

At this point, we can return to examine more closely the original assumption underlying FIG. 4, namely, that "for some reason, the distance between the drumhead 13 and the transducers 11 and 72 is suddenly, slightly reduced." This sudden reduction (or likewise an enlargement), in practice, can result from actual physical movement, or from other factors in the external environment such as a change in temperature. When this system is set up initially for a given detection, this eliminates the need to be concerned about the exact distance between the transducers 11 and 12 and the vibrating surface 73, because this self-aligning/calibrating feature, no matter what the variation in distance, will 1) generate a deviation signal 220 such as in FIG. 4 showing how far the system is out of alignment, and 2) recalibrate back toward the proper calibration of FIG. 3 by shifting reference signal 206 accordingly via the self-adjustment/calibration means comprising, in this embodiment, gating logic 222, up/down counter 224 and delay device 226. Calibration is automatic (self-aligning), and thus setup is extremely simplified.

This self-aligning feature allows the sensor automatically work properly over a wide range of setup dimensions and allows it to continue to operate properly even subject to changing air temperature and other factors, and without placing any special, separate "target" on the drumhead.

Figure 5:
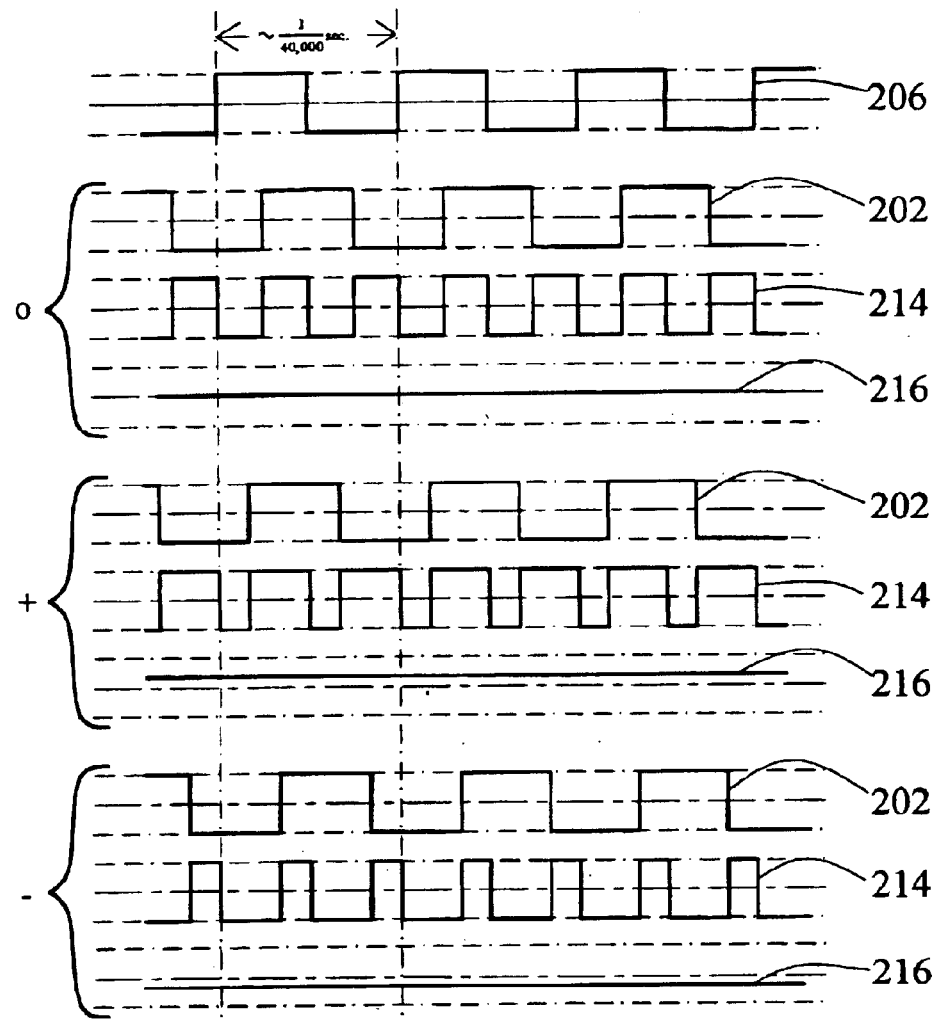
FIG. 5 illustrates the signals at various junctures of the circuit of FIG. 2, when the drumhead or similar surface is vibrating.

FIG. 5 illustrates the reference signal 206, reflected signal 202, comparison signal 214, and representation signal 216 inherently produced by the circuit of FIG. 2, when the drumhead or similar surface is vibrating, and assuming proper calibration in accordance with the discussion of FIG. 4. In this discussion, it is assumed that vibrating surface 13 (e.g., the drumhead) is vibrating at a frequency of 1 kHz or less, i.e., at a cycle time of 1 cycle per 1/1000 second or longer, as illustrated toward the right-hand side of FIG. 1. For sake of discussion, we shall assume that the drumhead vibrates at 0.5 kHz, that it moves from "o" to "+" to "o" to "−" and back to "+" every 1/500 second. Since the transducer is operating at 40 kHz, i.e., at 80 times this frequency of the drumhead, it can also be assumed that when the drumhead peaks at "+" and is thus closest to the transducer, valleys as "−" and is thus farthest from the transducer, or is moving through "o" at the quiescent position, the drumhead may be approximated as substantially stationary over several transducer cycles.

Figure 6:
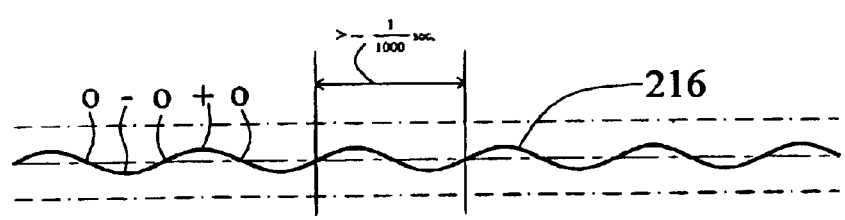
FIG. 6 illustrates how the various signals in FIG. 5 are used to detect the vibrational movement of the vibrating surface, which serves as the basis for displaying information pertaining the said vibrational movement.

In FIG. 5, the upper triplet of signals designated by "o," shows the drumhead (13) at "o" over the several transducer cycles for which the "substantially stationary at o" approximation is accurate. As discussed in connection with FIG. 3, this means that comparison signal 214 is high half the time and low half the time, and that its average value emerging from low pass filter 212 as representation signal 216 will be the quiescent value "o." The middle triplet of signals designated by "+," shows the drumhead (13) at "+" over the several transducer cycles for which the "substantially stationary at +" approximation is accurate. Here, as discussed in connection with FIG. 4, the closer proximity of drumhead 13 to transducers 11 and 12 will return reflected signal 202 to receiving transducer 12 slightly sooner than occurs when the drumhead 13 is in the "o" position. Thus, comparison signal 214 is higher more of the time and lower less of the time, such that its average value emerging from low pass filter 212 as representation signal 216 will be somewhat higher than "o." Finally, the lower triplet of signals designated by "−," shows the drumhead (13) at "−" over the several transducer cycles for which the "substantially stationary at −" approximation is accurate. In this situation, for all of the reasons discussed before, the average value of the comparison signal 214 emerging from low pass filter 212 as representation signal 216 will be somewhat lower than "o." Of course, if one combines the representation signal 216 shown in FIG. 5 over several cycles from "o" to "+" to "o" to "−" to "o," and looks at a longer period of time greater than 1/1000 second, it is clear that representation signal will cycle right along with the movement of vibrating surface (e.g., drumhead) 13, as shown in FIG. 6. That is, representation signal 216, which is an electronic signal inherently generated by the circuitry of FIG. 2, will precisely track and represent the actual vibrational movement 15 of the vibrating surface (e.g., drumhead) 13, as illustrated in FIG. 1. Thus, representation signal 216 is an electronic reconstruction from the ultrasonic emission 11 and reception 12, of the vibrational movement 15 of vibrating surface 13, which is the desired signal output of the overall system. By feeding representation signal 216 to vibrational information display device 228, one can then display information about these vibrations to the end user in whatever human-readable manner is desired.

Having reviewed FIGS. 3 through 6, a final comment is in order about the low pass filter 212 and the low-low pass filter 218. When the vibrating surface 13 is vibrating, it is low pass filter 212 that sifts out the representation signal 216 which is the electronic reconstruction of the vibrational movement 15 of vibrating surface 13. If the overall calibration should happen to drift high or low away from "o," the center of representation signal 216 will also drift high or low accordingly, but will be masked by the oscillations up to 1 kHz (or whatever magnitude of filtration is set by low pass filter 212). That is where low-low pass filter 218 comes in, which is 1 Hz for the illustrated embodiment but need not be limited to 1 Hz. Because low-low pass filter 218 filters at a frequency lower than the vibrational frequencies of interest, the frequencies between 1 Hz and 1 kHz will also be masked out, and all that will remain is the center line of representation signal 216, with its slight upward or downward drift, but without all the 1 Hz to 1 kHz oscillations. This will allow for continuous, automatic recalibration (self-alignment) of the overall system, not only at initial setup, but also throughout operation in response to any and all environmental changes.

It is also important to understand that this device, system and method is used to detect two types of movement of surface 13. First, the representation signal 216 emerging from low pass filter 212 represents the detection of the vibration of surface 13, which is generally a form of periodic movement, and is the movement that it is ultimately desired to detect and present (e.g., through display device 228) to the end user. Second, deviation signal 220 emerging from low-low pass filter 218 represents the detection of gross movement of surface 13, which is generally not periodic, but rather is generally motion due to gross relative movement between the ultrasonic transducers 11, 12 and surface 13. This motion is not presented to the end user per se, but is used to self-calibrate the system to ensure accuracy in the presentation of the periodic movement.

This sensing system provides significantly more latitude to place the sensor further from the drumhead as noted above, up to three or more feet away—and eliminates the need to place a special separate "target" on the drumhead itself. This is because the ultrasonic waves are not compromised by ambient light or other radiation, or by ambient sound, and will reflect from a surface whether that surface is optically transparent, translucent, or opaque. Additionally, this system requires very little current, and so can powered by a battery requiring only infrequent recharging or replacement.

In essence, the embodiments herein described employ an ultrasonic interferometer for vibration sensing generally and drum head or tunable instrument vibration sensing specifically, and are made most practical and useful by the unique self-aligning feature described herein.

Beyond sensing drumhead and tunable instrument vibrations, this invention has applications generally for non-contact vibration sensing of surfaces, such as, but not limited to, machine elements.

While only certain preferred features of the invention have been illustrated and described, many modifications and changes will occur to those skilled in the art. It is, therefore, to be understood that the appended claims are intended to cover all such modifications and changes as fall within the true spirit of the invention.

What is claimed is:

1. A method for sensing of vibration of a surface (13), comprising the steps of:
    generating a comparison signal (214) by exclusive or comparing (210) a reflected signal (202) representing ultrasonic radiation (14) as received (12) following a reflection of said ultrasonic radiation (14) off of said surface (13), with a reference signal (206) representing said ultrasonic radiation (14) as emitted (11) toward said surface (13); and
    extracting a representation signal (216) by passing through from said comparison signal (214), frequencies lower than a low pass threshold (212).

2. The method of claim 1, additionally for self-calibrating said sensing of said vibration of said surface (13), further comprising the steps of:
    extracting a deviation signal (220) by passing through from said comparison signal (214), frequencies lower than a low-low pass threshold (218); and
    maintaining said deviation signal (220) in a substantially quiescent state and thereby self-calibrating said sensing, by shifting (222, 224, 226) said reference signal (206) relative to said reflected signal (202) in response to said deviation signal (220) straying from said substantially quiescent state.

3. The method of claim 1, further comprising the step of:
    displaying (228) information pertaining to said vibration of said surface (13), based on said representation signal (216).

4. The method of claim 2, further comprising the step of:
    displaying (228) information pertaining to said vibration of said surface (13), based on said representation signal (216).

5. The method of claim 3, said step of displaying (228) information pertaining to said vibration of said surface (13) further comprising the steps of:

displaying one of the alphabetic characters A, B, C, D, E, F and G representing a musical note corresponding with said vibration of said surface (13);

displaying a musical sharp note indicator if said musical note is sharp;

displaying a musical flat note indicator if said musical note is flat; and displaying a degree to which said musical note is out of tune.

6. The method of claim 4, said step of displaying (228) information pertaining to said vibration of said surface (13) further comprising the steps of:

displaying one of the alphabetic characters A, B, C, D, E, F and G representing a musical note corresponding with said vibration of said surface (13);

displaying a musical sharp note indicator if said musical note is sharp;

displaying a musical flat note indicator if said musical note is flat; and displaying a degree to which said musical note is out of tune.

7. The method of claim 1, said surface (13) comprising a drumhead.

8. The method of claim 2, said surface (13) comprising a drumhead.

9. The method of claim 1, further comprising the steps of:

emitting (11) said ultrasonic radiation (14) toward said surface (13) using an emitting ultrasonic transducer (11); and receiving (12) said ultrasonic radiation (14) following said reflection off of said surface (13) using a receiving ultrasonic transducer (12).

10. The method of claim 2, further comprising the steps of:

emitting (11) said ultrasonic radiation (14) toward said surface (13) using an emitting ultrasonic transducer (11); and receiving (12) said ultrasonic radiation (14) following said reflection off of said surface (13) using a receiving ultrasonic transducer (12).

11. The method of claim 1, further comprising the steps of:

emitting (11) said ultrasonic radiation (14) toward said surface (13) at a frequency at least approximately ten times as high as a highest vibrational frequency of interest of said surface (13).

12. The method of claim 2, further comprising the steps of:

emitting (11) said ultrasonic radiation (14) toward said surface (13) at a frequency at least approximately ten times as high as a highest vibrational frequency of interest of said surface (13).

13. The method of claim 9, further comprising the steps of:

locating said ultrasonic transducers (11,12) at least approximately 5 mm. away from said surface (13); and locating said ultrasonic transducers (11,12) at most approximately 1 m. away from said surface (13).

14. The method of claim 10, further comprising the steps of:

locating said ultrasonic transducers (11,12) at least approximately 5 mm. away from said surface (13); and locating said ultrasonic transducers (11,12) at most approximately 1 m. away from said surface (13).

15. The method of claim 9, further comprising the steps of:

locating said ultrasonic transducers (11,12) at least approximately 2.5 cm. away from said surface (13); and locating said ultrasonic transducers (11,12) at most approximately 20 cm. away from said surface (13).

16. The method of claim 14, further comprising the steps of:

locating said ultrasonic transducers (11,12) at least approximately 2.5 cm. away from said surface (13); and locating said ultrasonic transducers (11,12) at most approximately 20 cm. away from said surface (13).

17. The method of claim 9, further comprising the step of said emitting transducer (11) focusing said ultrasonic radiation (11) to cover substantially a single spot on said surface (13).

18. The method of claim 10, further comprising the step of said emitting transducer (11) focusing said ultrasonic radiation (11) to cover substantially a single spot on said surface (13).

19. A method for self-calibrating a sensing of vibration of a surface (13), comprising the steps of:

generating a comparison signal (214) by comparing (210) a reflected signal (202) representing ultrasonic radiation (14) as received (12) following a reflection of said ultrasonic radiation (14) off of said surface (13), with a reference signal (206) representing said ultrasonic radiation (14) as emitted (11) toward said surface (13);

extracting a deviation signal (220) by passing through from said comparison signal (214), frequencies lower than a low-low pass threshold (218); and maintaining said deviation signal (220) in a substantially quiescent state and thereby self-calibrating said sensing, by shifting (222, 224, 226) said reference signal (206) relative to said reflected signal (202) in response to said deviation signal (220) straying from said substantially quiescent state.

20. The method of claim 19, additionally for said sensing of said vibration of said surface (13), further comprising the step of:

extracting a representation signal (216) by passing through from said comparison signal (214), frequencies lower than a low pass threshold (212).

21. The method of claim 20, further comprising the step of:

displaying (228) information pertaining to said vibration of said surface (13), based on said representation signal (216).

22. The method of claim 21, said step of displaying (228) information pertaining to said vibration of said surface (13) further comprising the steps of:

displaying one of the alphabetic characters A, B, C, D, E, F and G representing a musical note corresponding with said vibration of said surface (13);

displaying a musical sharp note indicator if said musical note is sharp;

displaying a musical flat note indicator if said musical note is flat; and displaying a degree to which said musical note is out of tune.

23. The method of claim 19, said surface (13) comprising a drumhead.

24. The method of claim 20, said surface (13) comprising a drumhead.

25. The method of claim 19, further comprising the steps of:
- emitting (11) said ultrasonic radiation (14) toward said surface (13) using an emitting ultrasonic transducer (11); and
- receiving (12) said ultrasonic radiation (14) following said reflection off of said surface (13) using a receiving ultrasonic transducer (12).

26. The method of claim 20, further comprising the steps of:
- emitting (11) said ultrasonic radiation (14) toward said surface (13) using an emitting ultrasonic transducer (11); and
- receiving (12) said ultrasonic radiation (14) following said reflection off of said surface (13) using a receiving ultrasonic transducer (12).

27. The method of claim 19, further comprising the steps of:
- emitting (11) said ultrasonic radiation (14) toward said surface (13) at a frequency at least approximately ten times as high as a highest vibrational frequency of interest of said surface (13).

28. The method of claim 20, further comprising the steps of:
- emitting (11) said ultrasonic radiation (14) toward said surface (13) at a frequency at least approximately ten times as high as a highest vibrational frequency of interest of said surface (13).

29. The method of claim 25, further comprising the steps of:
- locating said ultrasonic transducers (11,12) at least approximately 5 mm. away from said surface (13); and
- locating said ultrasonic transducers (11,12) at most approximately 1 m. away from said surface (13).

30. The method of claim 26, further comprising the steps of:
- locating said ultrasonic transducers (11,12) at least approximately 5 mm. away from said surface (13); and
- locating said ultrasonic transducers (11,12) at most approximately 1 m. away from said surface (13).

31. The method of claim 25, further comprising the steps of:
- locating said ultrasonic transducers (11,12) at least approximately 2.5 cm. away from said surface (13); and
- locating said ultrasonic transducers (11,12) at most approximately 20 cm. away from said surface (13).

32. The method of claim 26, further comprising the steps of:
- locating said ultrasonic transducers (11,12) at least approximately 2.5 cm. away from said surface (13); and
- locating said ultrasonic transducers (11,12) at most approximately 20 cm. away from said surface (13).

33. The method of claim 25, further comprising the step of said emitting transducer (11) focusing said ultrasonic radiation (11) to cover substantially a single spot on said surface (13).

34. The method of claim 26, further comprising the step of said emitting transducer (11) focusing said ultrasonic radiation (11) to cover substantially a single spot on said surface (13).

35. An apparatus for sensing of vibration of a surface (13), comprising:
- comparator means (210) for generating a comparison signal (214) by comparing (210) a reflected signal (202) representing ultrasonic radiation (14) as received (12) following a reflection of said ultrasonic radiation (14) off of said surface (13), with a reference signal (206) representing said ultrasonic radiation (14) as emitted (11) toward said surface (13); and
- low pass filter means (212) for extracting a representation signal (216) by passing through from said comparison signal (214), frequencies lower than a low pass threshold (212).

36. The apparatus of claim 35, additionally for self-calibrating said sensing of said vibration of said surface (13), further comprising:
- low-low pass filter means (218) for extracting a deviation signal (220) by passing through from said comparison signal (214), frequencies lower than a low-low pass threshold (218); and
- self-calibration means (222, 224, 226) for maintaining said deviation signal (220) in a substantially quiescent state and thereby self-calibrating said sensing, by shifting (222, 224, 226) said reference signal (206) relative to said reflected signal (202) in response to said deviation signal (220) straying from said substantially quiescent state.

37. The apparatus of claim 35, further comprising:
- display means (228) for displaying (228) information pertaining to said vibration of said surface (13), based on said representation signal (216).

38. The apparatus of claim 36, further comprising:
- display means (228) for displaying (228) information pertaining to said vibration of said surface (13), based on said representation signal (216).

39. The apparatus of claim 37, said display means (228) further comprising:
- note indicator means for displaying one of the alphabetic characters A, B, C, D, E, F and G representing a musical note corresponding with said vibration of said surface (13);
- sharp note indicator means for displaying a musical sharp note indicator if said musical note is sharp;
- flat note indicator means for displaying a musical flat note indicator if said musical note is flat; and
- out-of-tune indicator means displaying a degree to which said musical note is out of tune.

40. The apparatus of claim 38, said display means (228) further comprising:
- note indicator means for displaying one of the alphabetic characters A, B, C, D, E, F and G representing a musical note corresponding with said vibration of said surface (13);
- sharp note indicator means for displaying a musical sharp note indicator if said musical note is sharp;
- flat note indicator means for displaying a musical flat note indicator if said musical note is flat; and
- out-of-tune indicator means displaying a degree to which said musical note is out of tune.

41. The apparatus of claim 35, said surface (13) comprising a drumhead.

42. The apparatus of claim 32, said surface (13) comprising a drumhead.

43. The apparatus of claim 35, further comprising:
- emitting ultrasonic transducer means (11) for emitting (11) said ultrasonic radiation (14) toward said surface (13); and
- receiving ultrasonic transducer means (12) for receiving (12) said ultrasonic radiation (14) following said reflection off of said surface (13).

44. The apparatus of claim 36, further comprising:
emitting ultrasonic transducer means (11) for emitting (11) said ultrasonic radiation (14) toward said surface (13); and
receiving ultrasonic transducer means (12) for receiving (12) said ultrasonic radiation (14) following said reflection off of said surface (13).

45. The apparatus of claim 35, further comprising:
emitting ultrasonic transducer means (11) for emitting (11) said ultrasonic radiation (14) toward said surface (13) at a frequency at least approximately ten times as high as a highest vibrational frequency of interest of said surface (13).

46. The apparatus of claim 36, further comprising:
emitting ultrasonic transducer means (11) for emitting (11) said ultrasonic radiation (14) toward said surface (13) at a frequency at least approximately ten times as high as a highest vibrational frequency of interest of said surface (13).

47. The apparatus of claim 43, wherein:
said ultrasonic transducers (11,12) are located at least approximately 5 mm. away from said surface (13); and
said ultrasonic transducers (11,12) are located at most approximately 1 m. away from said surface (13).

48. The apparatus of claim 44, wherein:
said ultrasonic transducers (11,12) are located at least approximately 5 mm. away from said surface (13); and
said ultrasonic transducers (11,12) are located at most approximately 1 m. away from said surface (13).

49. The apparatus of claim 43, wherein:
said ultrasonic transducers (11,12) are located at least approximately 2.5 cm. away from said surface (13); and
said ultrasonic transducers (11,12) are located at most approximately 20 cm. away from said surface (13).

50. The apparatus of claim 44, wherein:
said ultrasonic transducers (11,12) are located at least approximately 2.5 cm. away from said surface (13); and
said ultrasonic transducers (11,12) are located at most approximately 20 cm. away from said surface (13).

51. The apparatus of claim 43, said emitting transducer means (11) focusing said ultrasonic radiation (11) to cover substantially a single spot on said surface (13).

52. The apparatus of claim 44, said emitting transducer means (11) focusing said ultrasonic radiation (11) to cover substantially a single spot on said surface (13).

53. An apparatus for self-calibrating a sensing of vibration of a surface (13), comprising:
comparator means (210) for generating a comparison signal (214) by comparing (210) a reflected signal (202) representing ultrasonic radiation (14) as received (12) following a reflection of said ultrasonic radiation (14) off of said surface (13), with a reference signal (206) representing said ultrasonic radiation (14) as emitted (11) toward said surface (13);
low-low pass filter means (218) for extracting a deviation signal (220) by passing through from said comparison signal (214), frequencies lower than a low-low pass threshold (218); and
self-calibration means (222, 224, 226) for maintaining said deviation signal (220) in a substantially quiescent state and thereby self-calibrating said sensing, by shifting (222, 224, 226) said reference signal (206) relative to said reflected signal (202) in response to said deviation signal (220) straying from said substantially quiescent state.

54. The apparatus of claim 53, additionally for said sensing of said vibration of said surface (13), further comprising:
low pass filter means (212) for extracting a representation signal (216) by passing through from said comparison signal (214), frequencies lower than a low pass threshold (212).

55. The apparatus of claim 54, further comprising:
display means (228) for displaying (228) information pertaining to said vibration of said surface (13), based on said representation signal (216).

56. The apparatus of claim 55, said display means (228) further comprising:
note indicator means for displaying one of the alphabetic characters A, B, C, D, E, F and G representing a musical note corresponding with said vibration of said surface (13);
sharp note indicator means for displaying a musical sharp note indicator if said musical note is sharp;
flat note indicator means for displaying a musical flat note indicator if said musical note is flat; and
out-of-tune indicator means displaying a degree to which said musical note is out of tune.

57. The apparatus of claim 53, said surface (13) comprising a drumhead.

58. The apparatus of claim 54, said surface (13) comprising a drumhead.

59. The apparatus of claim 53, further comprising:
emitting ultrasonic transducer means (11) for emitting (11) said ultrasonic radiation (14) toward said surface (13); and
receiving ultrasonic transducer means (12) for receiving (12) said ultrasonic radiation (14) following said reflection off of said surface (13).

60. The apparatus of claim 54, further comprising:
emitting ultrasonic transducer means (11) for emitting (11) said ultrasonic radiation (14) toward said surface (13); and
receiving ultrasonic transducer means (12) for receiving (12) said ultrasonic radiation (14) following said reflection off of said surface (13).

61. The apparatus of claim 53, further comprising:
emitting ultrasonic transducer means (11) for emitting (11) said ultrasonic radiation (14) toward said surface (13) at a frequency at least approximately ten times as high as a highest vibrational frequency of interest of said surface (13).

62. The apparatus of claim 54, further comprising:
emitting ultrasonic transducer means (11) for emitting (11) said ultrasonic radiation (14) toward said surface (13) at a frequency at least approximately ten times as high as a highest vibrational frequency of interest of said surface (13).

63. The apparatus of claim 59, wherein:
said ultrasonic transducers (11,12) are located at least approximately 5 mm. away from said surface (13); and
said ultrasonic transducers (11,12) are located at most approximately 1 m. away from said surface (13).

64. The apparatus of claim 60, wherein:
said ultrasonic transducers (11,12) are located at least approximately 5 mm. away from said surface (13); and
said ultrasonic transducers (11,12) are located at most approximately 1 m. away from said surface (13).

65. The apparatus of claim 59, wherein:
said ultrasonic transducers (11,12) are located at least approximately 2.5 cm. away from said surface (13); and said ultrasonic transducers (11,12) are located at most approximately 20 cm. away from said surface (13).

66. The apparatus of claim 60, wherein:
said ultrasonic transducers (11,12) are located at least approximately 2.5 cm. away from said surface (13); and
said ultrasonic transducers (11,12) are located at most approximately 20 cm. away from said surface (13).

67. The apparatus of claim 59, said emitting transducer means (11) focusing said ultrasonic radiation (11) to cover substantially a single spot on said surface (13).

68. The apparatus of claim 60, said emitting transducer means (11) focusing said ultrasonic radiation (11) to cover substantially a single spot on said surface (13).

* * * * *